US008786398B2

(12) United States Patent
Wegelin et al.

(10) Patent No.: US 8,786,398 B2
(45) Date of Patent: Jul. 22, 2014

(54) DISPENSER WITH USE-BASED CONTENT DELIVERY

(75) Inventors: Jackson W. Wegelin, Stow, OH (US); Patrick J. O'Keefe, Jr., Wellington, OH (US); Andrew A. Moore, Wakeman, OH (US)

(73) Assignee: GOJO Industries, Inc., Akron, OH (US)

( * ) Notice: Subject to any disclaimer, the term of this patent is extended or adjusted under 35 U.S.C. 154(b) by 331 days.

(21) Appl. No.: 13/073,071

(22) Filed: Mar. 28, 2011

(65) Prior Publication Data

US 2012/0249331 A1 Oct. 4, 2012

(51) Int. Cl.
*G05B 23/02* (2006.01)

(52) U.S. Cl.
USPC ........................................ 340/3.1; 340/573.1

(58) Field of Classification Search
CPC .. G08B 19/76; G07F 9/02; A47K 2010/3226; A47K 5/1217; G06Q 30/02; G06Q 30/268
USPC ...................................................... 340/573.1
See application file for complete search history.

(56) References Cited

U.S. PATENT DOCUMENTS

| 6,375,038 B1 | 4/2002 | Daansen et al. | |
|---|---|---|---|
| 7,411,511 B2 | 8/2008 | Kennish et al. | |
| 7,774,096 B2 | 8/2010 | Goerg et al. | |
| 7,791,490 B2 | 9/2010 | Kennish et al. | |
| 2007/0261077 A1* | 11/2007 | Zalewski et al. | 725/35 |
| 2008/0021779 A1* | 1/2008 | Lynn et al. | 705/14 |
| 2009/0091458 A1 | 4/2009 | Deutsch | |
| 2010/0123560 A1 | 5/2010 | Nix et al. | |

FOREIGN PATENT DOCUMENTS

| WO | 2005065509 A1 | 7/2005 |
|---|---|---|
| WO | 2006135922 A2 | 12/2006 |

* cited by examiner

*Primary Examiner* — Travis Hunnings
(74) *Attorney, Agent, or Firm* — Renner, Kenner, Greive, Bobak, Taylor & Weber

(57) ABSTRACT

A dispenser with use-based content delivery includes an indicator to present audio and/or video content that is delivered from a remote computer via a wired or wireless network. In addition, the dispenser is configured to monitor various operation parameters associated with the dispenser, as well as the physical attributes of its users. The dispenser uses such data to select informational content that targets the needs of each specific user, so as to communicate informational content in a highly-effective manner.

9 Claims, 2 Drawing Sheets

DISPENSER WITH USE-BASED CONTENT DELIVERY

TECHNICAL FIELD

The present invention generally relates to dispensers that dispense material, such as soap. Particularly, the present invention relates to a dispenser that automatically delivers informational content to a user, based on various operating parameters of the dispenser and/or based on at least one physical attribute of the user of the dispenser. More particularly, the present invention relates to dispensers that acquire audio and/or video content from a remote computer for presentation at the dispenser.

BACKGROUND OF THE INVENTION

The public has become increasingly concerned with disease and its transmission, and as such, there is a heightened level of awareness of the importance of cleansing and hygiene in general. For example, with respect to the transmission of *E. coli* in the food services industry, the rhinovirus in elementary schools, and nosocomial diseases within healthcare facilities, numerous studies have cited hand hygiene as an effective measure to guard against disease transmission. In response, the health care industry, the food services industry, and the hotel and travel industries have been forced to examine their protocols and procedures to ensure that their personnel are adopting hand sanitizing habits that are efficacious in the prevention of disease transmission.

In an effort to provide sufficient opportunities for individuals to have access to soap and sanitizers, many institutions and industries have increased the number of installed dispensers. As such, soap and sanitizer dispensers are now ubiquitous in our environment, and they provide opportunities to communicate information, such as advertising, promotional, educational, or any other information to the users of the dispensers. However, such dispensers do not make use of such opportunities to provide informational content to its users. Moreover, entities such as an airports and hospitals would have significant difficulty in managing the logistics involved in making informational content available at a large number of dispensers. In addition, because of the large amount of advertising and promotional material that is available, individuals have become very adept at ignoring information that does not pertain or have relevance to them in some compelling way. That is, if the communication of information content is not tailored or does not target the individual in some way, the information is largely or to a great extent ignored, which is unwanted.

Therefore, there is a need for a dispenser with use-based content delivery that is capable of presenting informational content, based on one or more operating parameters of the dispenser. Furthermore, there is a need for a dispenser with use-based content delivery that is capable of presenting informational content based on one or more physical attributes of the user. Still yet, there is a need for a dispenser with use-based content delivery that presents audio and/or video-based content that is acquired from a remote computer over a wired or wireless network.

SUMMARY OF THE INVENTION

In light of the foregoing, it is a first aspect of the present invention to provide a dispenser with use-based content delivery.

It is another aspect of the present invention to provide a dispenser for dispensing material from a refill container to a user, the dispenser comprising a controller configured to store an identification code; a pump coupled to said controller, said pump adapted to be in fluid communication with the refill container; an actuator coupled to said controller, such that when said actuator is engaged, said pump dispenses material from the refill container; an indicator coupled to said controller; and a transceiver coupled to said controller, said transceiver configured to receive content that is associated with said identification code for presentation at said indicator.

A further aspect of the present invention is to provide a dispenser for dispensing material from a refill container to a user, the dispenser comprising a controller; a pump coupled to said controller, said pump adapted to be in fluid communication with the refill container; an actuator coupled to said controller, such that when said actuator is engaged, said pump dispenses material from the refill container; an indicator coupled to said controller; and a transceiver coupled to said controller, said transceiver configured to receive content stored at a remote computer, wherein said controller transmits at least one operating parameter associated with the dispenser to said remote computer, such that said indicator presents said content from said remote computer that is based on said at least one operating parameter.

Yet another aspect of the present invention is to provide a dispenser for dispensing material from a refill container to a user, the dispenser comprising a controller; a pump coupled to said controller, said pump adapted to be in fluid communication with the refill container; an actuator coupled to said controller, such that when said actuator is engaged, said pump dispenses material from the refill container; a sensor coupled to said controller, said sensor configured to identify at least one physical attribute associated with the user; an indicator coupled to said controller; and a transceiver coupled to said controller, said transceiver configured to receive content stored at a remote computer, wherein said controller transmits a reference identifier based on said at least one physical attribute to the remote computer to receive content based on said reference identifier at said transceiver for presentation by said indicator.

BRIEF DESCRIPTION OF THE DRAWINGS

These and other features and advantages of the present invention will become better understood with regard to the following description, appended claims, and accompanying drawings where:

DETAILED DESCRIPTION OF THE INVENTION

Figure 1:
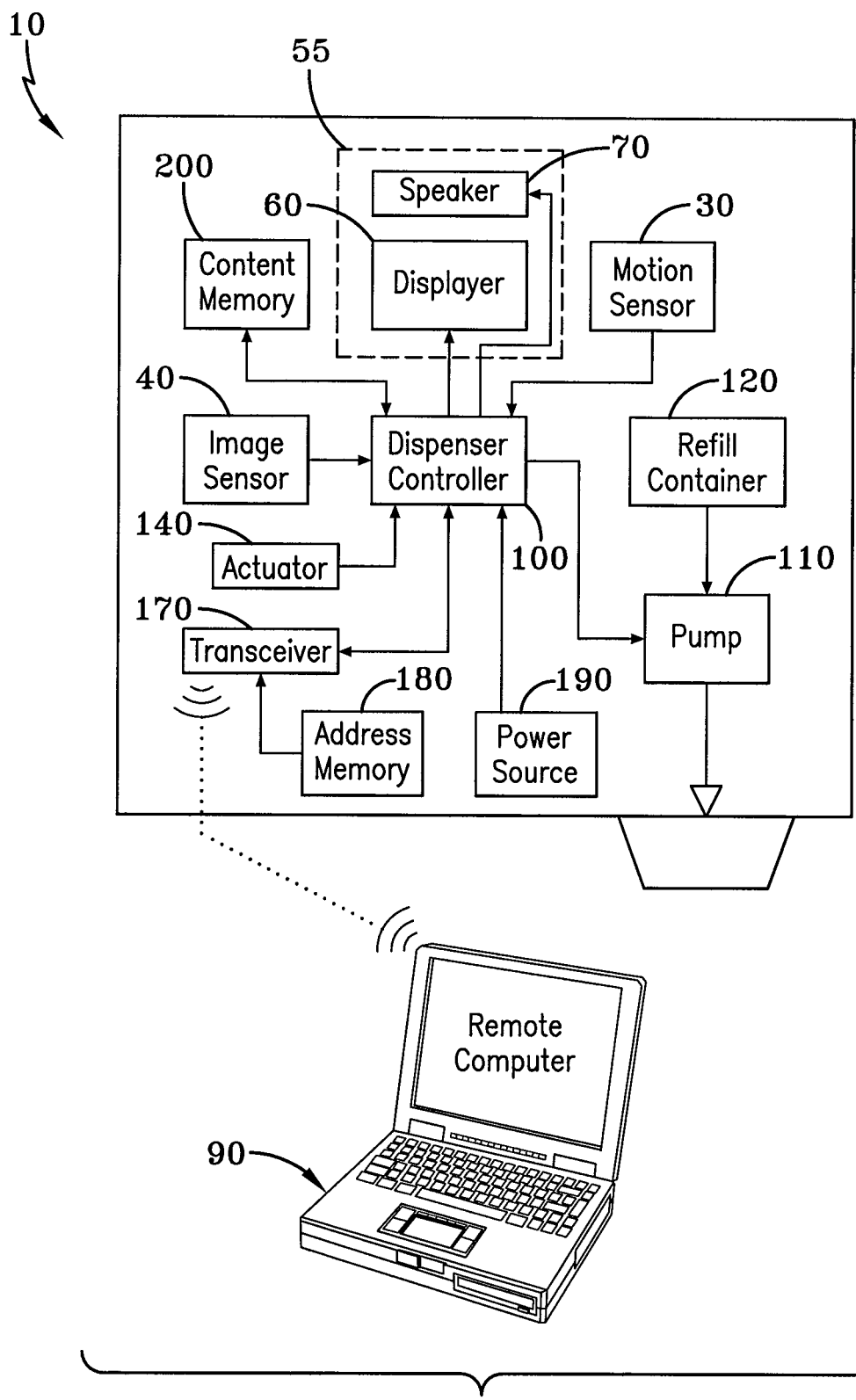
FIG. 1 is a block diagram showing a dispenser having use-based content delivery in accordance with the concepts of the present invention.

A dispenser with use-based content delivery is generally referred to by the numeral 10, as shown in FIG. 1 of the drawings. The dispenser 10 includes a motion sensor 30 and an image sensor 40 that are configured to detect one or more physical attributes or features of the user, such as body size, height, body dimensions, and facial dimensions, as well as the motion of any of their body parts, such as their arms, for example. After identifying one or more of the physical attributes of the user, the dispenser 10 presents content data that is based on such physical attributes, either in audible and/or visual form, via an indicator 55, which comprises a display 60 and/or speaker 70. In addition to identifying physical attributes of users, the dispenser 10 is also configured to monitor various operating parameters associated with the dispenser's operation, including the time of day and usage patterns of the dispenser 10, to determine the specific informational content to present via the indicator 55. For the purposes of the following discussion, the terms "content" or "informational content" include any audible and/or visual information, such as advertising and promotion information, education information, location information, instructions or messages that are specific to one or more dispensers 10 (e.g. "wash-don't sanitize"), and the like, for example. Moreover, the dispenser 10 retrieves the informational content over a wired or wireless communication network, such as a WIFI network, from a remote computer 90, thus facilitating the dissemination of informational content to a plurality of dispensers 10, such as in the case of an airport or other institution where multiple dispensers 10 are installed. As such, the dispenser 10 is able to dynamically present informational content that is targeted to the specific needs of the user of the dispenser 10, thus making the communication of any messages provided by the informational content more effective and valuable to the user of the dispenser 10.

Specifically, the dispenser 10 includes a dispenser controller 100 that includes the necessary hardware and/or software for carrying out the functions to be discussed. Coupled to the dispenser controller 100 is a pump 110 that is in fluid communication with a replaceable refill container 120 that is configured to carry any desired material, such as liquid material, which may include soap, sanitizer, or moisturizer, for example. An actuator 140 coupled to the dispenser controller 100 comprises any suitable button, switch, biometric sensor, or proximity sensor that is capable of identifying the presence of a user's hand or other portion of a user's body or is capable of being physically actuated by force applied by a user's hands or other body part. Thus, upon the engagement of the actuator 140 by the user, whereupon the user's hand or body portion are detected by the actuator 140 or the actuator 140 is physically actuated, the pump 110 is activated, and liquid material from the refill container 120 is dispensed therefrom.

The motion sensor 30 and the image sensor 40 are coupled to the dispenser controller 100 and may each comprise an infrared (IR) sensor, CCD (charge coupled device) sensor, or the like. Thus, the motion sensor 30 may comprise any suitable sensor that is capable of detecting the relative motion of the physical attributes or parts of a user's body of the dispenser 10 with suitable resolution, while the image sensor 40 may comprise any sensor that is capable of detecting static images of the physical attributes or traits of a user's body. For example, the motion sensor 30 is configured to identify the relative motion of any of the physical features or attributes of the user, such as his or her particular walking gait while approaching the dispenser 10, as well as his or her arm movements and facial movements. In addition, the image sensor 40 is configured to identify one or more physical features or attributes of a user, such as the size of the user's arms, torso, hands, and face, as well as the relative proportion of his or her facial features or other body part. Moreover, the term "physical attribute" as used herein includes any physical trait, attribute, or characteristic that is identifiable by the sensors 30,40. In addition, the motion sensor 30 and/or the image sensor 40 may be configured to identify the temperature or thermal image of a user as a physical attribute of the user, such as in the case when the motion sensor 30 and the image sensor 40 comprise an IR sensor. It should also be appreciated that the motion sensor 30 and the image sensor 40 may be combined into one sensor or maintained separately. In another aspect, the actuator 140 may comprise a motion sensor and/or an image sensor that are capable of providing image and motion detection functions discussed above without the need for the separate motion sensor 30 and image sensor 40.

The indicator 55 may comprise either the display 60 and/or the speaker 70, which are coupled to the dispenser controller 100. Specifically, the display 60 comprises any suitable display, such as an LCD (liquid crystal display) display, for displaying static or dynamic visual images that are provided by the informational content. In addition, the speaker 70 is configured to present any desired audio sound, such as a promotional message, that is provided by the informational content.

The dispenser 10 also provides a transceiver 170 that is coupled to the dispenser controller 100 that is capable of transmitting and receiving data from the remote computer 90. Specifically, the transceiver 170 is configured to transmit a reference identifier to the computer 90 and configured to receive informational content transmitted from the computer 90. Specifically, the reference identifier comprises data that includes operating parameters of the dispenser 10, as well as information that quantifies the physical attributes of the user that are imaged by the sensors 30,40, using any suitable technique. For example, the reference identifier may be computed by the controller 100 by numerically quantifying certain physical attributes of a person who is identified by the sensors 30,40 in a predetermined manner and then compared to a lookup table of reference identifiers stored at the controller 100 or remote computer 90 that are associated with predetermined informational content data. Thus, informational content that is targeted to the specific physical attributes of the user can be delivered to the user of the dispenser. That is, informational content, such as advertisements, promotions, and educational and health information that are relevant to specific persons can be identified and then communicated to the user of the dispenser. In addition, the dispenser controller 100 may be configured to monitor various operating parameters associated with the dispenser 10. For example, the operating parameters may include the time of day when the actuator 140 is engaged, as well as the pattern or frequency in which the actuator 140 has been engaged. Moreover, the operating parameters may also include the status of the refill container 120 (empty/full), the status of the power source 190 (low power/full power), the location of the dispenser 10 (room number), and the type (e.g. sanitizer, moisturizer, soap, etc.) of refill container 120 installed at the dispenser 10. As such, the time of day and the actuator 140 engagement patterns may be processed individually or in combination, using known techniques, by the dispenser controller 100 to generate a reference identifier to identify specific informational content for presentation via the indicator 55. Physical attributes and the operating parameters of the dispenser may be forwarded to the remote computer 90 and processed to generate a reference identifier that is used to identify the appropriate content to be forwarded to the dispenser 10.

The dispenser 10 and the remote computer 90 may communicate reference identifiers and informational content using any suitable wired or wireless communication network. For example, the dispenser 10 and remote computer 90 may communicate over a wired ETHERNET network or over a wireless communication network, such as a WIFI or BLUETOOTH network, using any suitable communication protocol, such as FTP (file transfer protocol). In addition, the dispenser 10 and the remote computer 90 may communicate using other communication networks and protocols, such as, but not limited to, ZIGBEE, HTP/HTTP (hypertext transfer protocol), RUBEE, PEANUT, IRDA, and cellular networks, including 3 G/4 G and LTE (long term evolution) cellular networks. It should also be appreciated that the dispenser 10 and the remote computer 90 may communicate using time-synchronized wireless networks, as well as femtocell-based cellular networks. Specifically, the computer 90 comprises any suitable computing device that has the necessary hardware and/or software for carrying out the functions to be discussed. In particular, the computer 90 includes the necessary storage to maintain the informational content for transmission to one or more dispensers 10 when requested thereby, such as in the case of when a reference identifier is sent to the computer 90. In addition, the dispenser 10 may include an address memory 180 that is coupled to the transceiver 170 that is configured to store a MAC (media access control) address or other identification address or code. Specifically, the MAC address is configured to uniquely identify the network interface provided by the dispenser 10, which is comprised of the transceiver 170; however, the identification address or code may be used to uniquely identify any component of the dispenser 10, such as the controller 100, or may be used to uniquely identify the dispenser 10 itself. As such, the remote computer 90 is able to communicate directly with specific dispensers 10 by identifying each dispenser 10 by its MAC address. Furthermore, it should be appreciated that the identification address or code may be stored directly at the controller 100 in lieu of the address memory 180.

The dispenser 10 is powered by any suitable power source 190, such as a battery, that is coupled to the dispenser controller 100. However, the power source 190 may comprise any other suitable source of power, such as a photovoltaic cell or a standard electrical wall outlet.

In addition, the dispenser 10 may also include a content memory 200 that is coupled to the dispenser controller 100 to temporarily and/or permanently store informational content received from the computer 90. For example, the content memory 200 may comprise any suitable volatile or non-volatile memory. As such, if specific content is to be presented on a frequent basis, the dispenser 10 may store the informational content received from the remote computer 90 in the content memory 200, so as to reduce the subsequent need for the dispenser 10 to access the remote computer 90 to acquire informational content based on the reference identifier. In addition, such operation reduces the consumption of power from the power source 190 of the dispenser 10, thereby extending its operating life.

Figure 2:
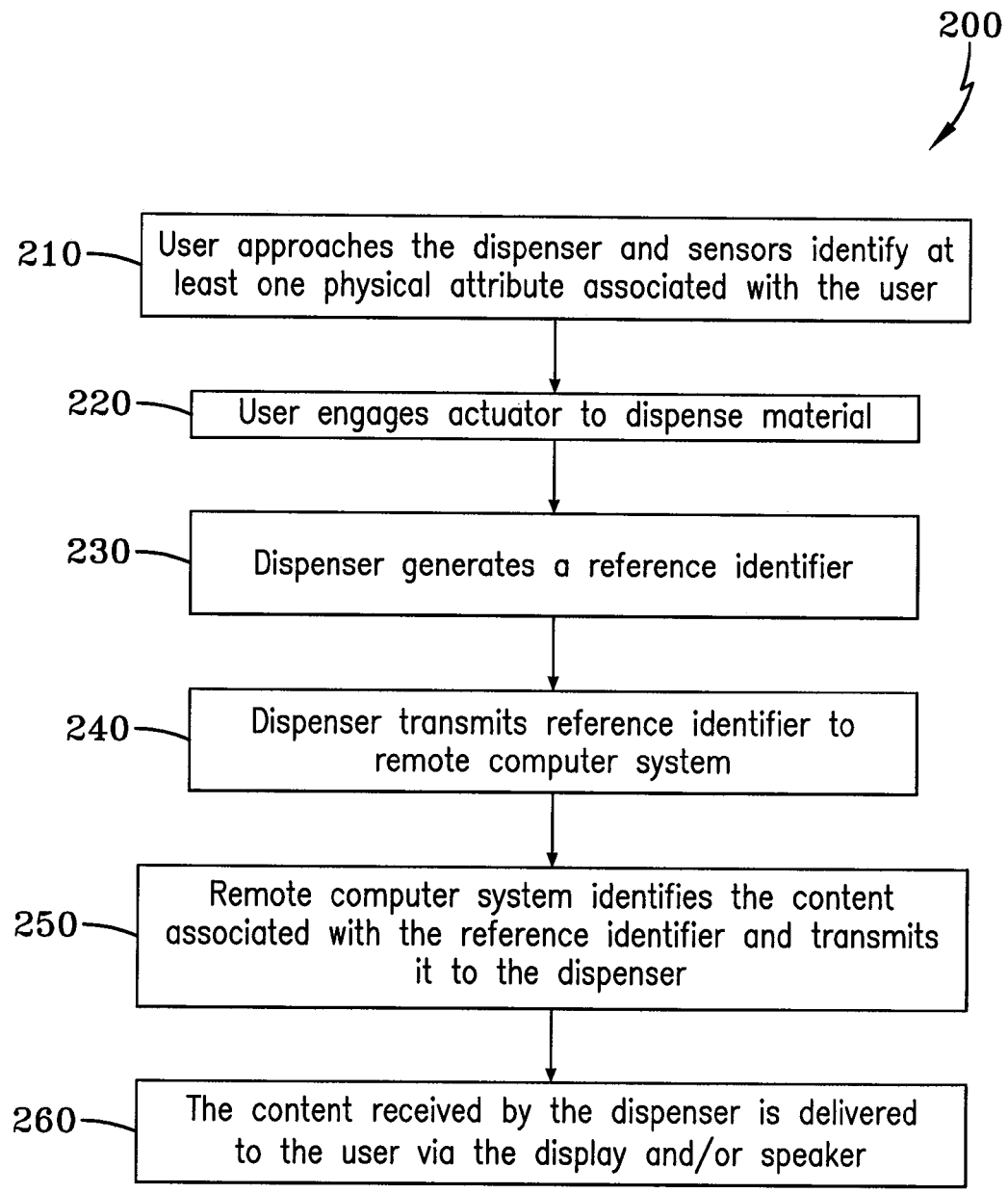
FIG. 2 is a flow diagram showing the operational steps taken by the dispenser when it is placed into use in accordance with the concepts of the present invention.

Thus, with the components of the dispenser 10 set forth, the operational steps associated with its operation, generally referred to by the numeral 200, will now be presented, as shown in FIG. 2 of the drawings. Initially at step 210, the motion and image sensors 30,40 are configured to identify at least one physical attribute associated with a person that approaches the dispenser 10. Next, at step 220, the user engages the actuator 140 to initiate the operation of the pump 110, so as to dispense material from the refill container 120. Upon the engagement of the actuator 140, the process continues to step 230, where the dispenser controller 100 processes the physical attributes of the user identified by the motion and image sensors 30,40 to generate a reference identifier that is associated with the particular informational content that is most relevant to the particular user of the dispenser 10. Alternatively, step 230 may process the operating parameters of the dispenser 10 identified by the dispenser controller 100 in order to generate a reference identifier, as well. It should also be appreciated that step 230 may be carried out such that the reference identifier is based on the combination of the physical attributes of the user and the operating parameters of the dispenser 10. Continuing, once the reference identifier is determined, using any suitable technique, the dispenser transmits the reference identifier to the remote computer system 90, as indicated at step 240. Next, at step 250, the computer 90 identifies the informational content associated with the received reference identifier and transmits it to the dispenser 10 via a wired or wireless network, such as a WIFI network. Once the content is received by the transceiver 170 of the dispenser 10, it is presented at the indicator 55 for presentation to the user via the display 60 and/or speaker 70, as indicated at step 260. As such, by identifying the specific physical attributes of a given user and/or the operating parameters of the dispenser 10, the dispenser 10 is able to provide highly-targeted informational content to that user, thus increasing the overall effectiveness of the communication, as the value of the information being delivered by the dispenser 10 is more compelling and meaningful to the user's needs.

It should also be appreciated that the process 200 may be carried out without steps 210 and 230, such that content presented by the indicator 55 of the dispenser 10 is based solely on the particular identification address or code associated with the dispenser 10. As such, the identification address or code may be transmitted to the remote computer 90 in lieu of the reference identifier at step 240. That is, content may be presented on the indicator 55 that is based or otherwise associated with an identification address or code of a given dispenser 10. As such, each dispenser 10 may be delivered differing content by the remote computer 90.

It will, therefore, be appreciated that one advantage of one or more embodiments of the present invention is that a dispenser with use-based content delivery allows targeted audible and/or visual content to be presented to a user that is based on the user's physical attributes. Another advantage of the present invention is that a dispenser with use-based content delivery allows targeted audible and/or visual content to be presented to a user, based on the operating parameters of the dispenser. Yet another advantage of the present invention is that the dispenser with use-based content delivery acquires content for dissemination at the dispenser from a remote computer using a wired or wireless network, such as a WIFI network.

Although the present invention has been described in considerable detail with reference to certain embodiments, other embodiments are possible. Therefore, the spirit and scope of the appended claims should not be limited to the description of the embodiments contained herein.

What is claimed is:

1. A dispenser for dispensing material from a refill container to a user, the dispenser comprising:
    a controller to monitor at least one operating parameter associated with the dispensing of the material;
    a pump coupled to said controller, said pump adapted to be in fluid communication with the refill container;
    an actuator coupled to said controller, such that when said actuator is engaged, said pump dispenses the material from the refill container;
    a sensor coupled to said controller, said sensor configured to anonymously identify at least one physical attribute associated with the user;
    an indicator coupled to said controller; and
    a transceiver coupled to said controller, said transceiver configured to receive content stored at a remote computer;
    wherein said controller transmits a reference identifier that includes both the anonymously identified at least one physical attribute and the at least one operating parameter associated with the dispensing of the material to the remote computer, whereupon the remote computer identifies and transmits content associated with both the anonymously identified at least one physical attribute and the at least one operating parameter associated with the dispensing of the material for receipt at said transceiver for presentation by said indicator.

2. The dispenser of claim 1, wherein said sensor comprises an image sensor.

3. The dispenser of claim 1, wherein said sensor comprises a motion sensor.

4. The dispenser of claim 1, wherein said indicator comprises a display.

5. The dispenser of claim 1, wherein said indicator comprises a speaker.

6. The dispenser of claim 1, wherein said transceiver receives said content from said remote computer via a wireless network.

7. The dispenser of claim 6, wherein said content is transferred via said wireless network using file transfer protocol (FTP).

8. The dispenser of claim 1, wherein said controller stores an identification code, such that said transceiver receives content only associated with said identification code.

9. The dispenser of claim 1, wherein said content is transferred via said wireless network using hyper-text transfer protocol (HTTP).

* * * * *